United States Patent [19]

Kigasawa et al.

[11] Patent Number: 4,572,832
[45] Date of Patent: Feb. 25, 1986

[54] SOFT BUCCAL

[75] Inventors: Kazuo Kigasawa; Hiroaki Shimizu, both of Tokyo; Toshihiro Hayashi, Chiba; Kazuo Watabe, Kanagawa; Akira Tanizaki, Tokyo; Osamu Koyama, Tokyo; Kikuo Wakisaka, Tokyo; Yasuaki Ogawa, Osaka, all of Japan

[73] Assignee: Grelan Pharmaceutical Co., Ltd., Tokyo, Japan

[21] Appl. No.: 540,161

[22] Filed: Oct. 7, 1983

[30] Foreign Application Priority Data

Oct. 7, 1982 [JP] Japan ................................ 57-175352
Sep. 20, 1983 [JP] Japan ................................ 58-172245

[51] Int. Cl.$^4$ ........................ A61K 9/20; A61K 9/22; A61K 47/00
[52] U.S. Cl. ................................ 424/19; 424/22; 424/81; 514/773; 514/774; 514/775
[58] Field of Search .................... 424/19–22, 424/DIG. 15, 81; 514/773, 774, 775

[56] References Cited

U.S. PATENT DOCUMENTS

| | | | |
|---|---|---|---|
| 4,059,686 | 11/1977 | Tanaka et al. | 424/81 |
| 4,250,163 | 2/1981 | Nagai et al. | 424/81 |
| 4,344,968 | 8/1982 | Aoada et al. | 424/81 |

FOREIGN PATENT DOCUMENTS

| | | | |
|---|---|---|---|
| 799450 | 11/1968 | Canada | 424/37 |
| 822075 | 9/1969 | Canada | 424/28 |
| 829269 | 12/1969 | Canada | 424/37 |
| 56-034619 | 4/1981 | Japan | 424/DIG. 15 |
| 56-100714 | 8/1981 | Japan | 424/28 |

OTHER PUBLICATIONS

Cyr C.A. 66, #118846w, (1967), of U.S. Pat. No. 3,312,594, 4/4/67.
Christenson et al., C.A. 75, #101284z, (1971) of U.S. Pat. No. 3,594,467, Jul. 20, 1971.
Teijin C.A. 94, #52962a, 59963b of JPN. 80118413 & 80118414, Sep. 11, 1980.

*Primary Examiner*—Shep K. Rose
*Attorney, Agent, or Firm*—Wegner & Bretschneider

[57] ABSTRACT

A soft buccal containing (1) a medicament to be absorbed through the oral mucosa, (2) a water-soluble protein, (3) a polyhydric alcohol, and (4) a fatty acid ester or/and a carboxyvinyl polymer, has various advantages such as good feeling in use, good retainability within the mouth, slow release, improved absorbability of drug through the mucosa, improved bioavailability, etc., and therefore can be used an excellent pharmaceutical preparation for administration to the mucous membrane of the mouth.

13 Claims, 4 Drawing Figures

SOFT BUCCAL

This invention relates to a pharmaceutical preparation in the form of soft buccals.

Known pharmaceutical preparations to be applied into the oral cavity include troches (lozenges), sublingual tablets, buccals (buccal tablets) and pastes. However, these preparations have various drawbacks. For instance, they are poor in agreeability and holdability in the mouth, the absorbability and bioavailability of the drug are low, and the drug efficacy is not durable. Thus, for instance, these preparations are hard to hold in the mouth for a prolonged period because a sense of incompatibility as produced in the mouth by the use thereof leads to crushing with the teeth, swallowing or disgorging. Moreover, the preparations are rapidly disintegrated in the oral cavity and accordingly they remain there only for a short period. As a result, a satisfactory drug efficacy duration cannot be expected. Furthermore, in relation to the bioavailability of drugs, no conventional preparations are satisfactory in absorbability through the oral mucosa as compared with oral administration. Under these circumstances, an oral cavity preparation free of such problems in the prior art has been waited for.

The present inventors made intensive researches in search of a novel oral cavity preparation improved in the points mentioned above and succeeded in developing an oral cavity preparation which is soft in feeling and good in agreeability in the mouth (hereinafter such oral cavity preparation having such characteristic features is sometimes referred to as "soft buccals") by incorporating a water-soluble protein and other things as a constituent of the base thereof, and the success has led to the completion of the present invention. Thus, the soft buccal provided according to this invention is a pharmaceutical preparation containing in the form of a soft buccal the following components (1), (2), (3) and (4), and is adapted to be held in complementary relation with the inner surface of the mouth. This invention has as its object to provide such a soft buccal.

(1) A medicament to be absorbed through the oral mucosa;

(2) a water-soluble protein having an absorption-promoting action;

(3) a polyhydric alcohol; and (4) a fatty acid ester or/and a carboxyvinyl polymer.

The drug to be incorporated in the soft buccals according to the present invention may be any drug which has adequate absorbability through the mucosa. Such drug is selected from among those drugs which act on the oral cavity (the site of application) and other organs or tissues than the mouth. The following are examples of such drugs:

(1) Drugs acting on the central nervous system (hypnotics or sedatives such as diazepam and estazolam; antiepileptics such as phenytoin, meprobamate and nitrazepam; antipyretic, analgesic and antiinflammatory agents such as acetaminophen, ethenzamide, salicylamide, pentazocine, clofezone, indomethacin, ketoprofen, flurbiprofen, diclofenac, clidanac, alclofenac, flufenamic acid, mefenamic acid, sulindac, piroxicam, menthol and camphor; D-penicillamine; corticoids; psychoneurotropic agents such as chlorpromazine; antivertigo agents such as isoprenaline, betahistine mesylate and scopolamine; general anesthetics; etc.);

(2) Drums acting on the peripheral nervous system (local anesthetics such as procaine and lidocaine; muscle relaxants such as triperizone hydrochloride, baclofen, dantrolene sodium and cyclobenzaprine hydrochloride; autonomic nervous system drugs; spasmolytics; etc.);

(3) Antiallergic agents or antihistaminics (diphenhydramine, periactin, etc.);

(4) Drugs for circulatory organs (cardiotonics such as digitalis and ubidecarenone; beta-blockers or anti arrhythmic agents such as pindolol and propranolol hydrochloride; diuretics such as theophylline, trichlormethiazide, spironolactone, methychlothiazide, metolazone, tripamide, furosemide and penflutizide; antihypertensive agents such as reserpine, clonidine hydrochloride, methyldopa, hydralazine, syrosingopine, rescinnamine, cinnarizine and prazocin hydrochloride; blood vessel-strengthening agents such as rutin and carbazochrome; vasoconstrictors such as dihydroergotamine mesylate and dihydroergotoxine mesylate; coronary vasodilators such as nitroglycerin, isosorbide dinitrate, dilazep hydrochloride, nifedipine, diltiazem hydrochloride, trimetazidine hydrochloride, trapidil and dipyridamole; peripheral vasodilators such as inositol hexanicotinate; antiarteriosclerotic agents such as clofibrate; pentoxifylline, cytochrome c, sodium dextransulfate, pyrithioxine, citicoline, nicardipine hydrochloride, dopamine hydrochloride, dobutamine hydrochloride, alprostadil, ifenprodil tartrate, etc.);

(5) Drugs for respiratory organs (antitussive and expectorant agents such as ephedrine, codeine and bromhexine; isoproterenol, dextromethorphan, orciprenaline, ipratropium bromide, cromoglicic acid, etc.);

(6) Drugs for digestive organs (peptic ulcer-treating agents such as allantoin, aldioxa, alcloxa, pirenzepine hydrochloride, secretin, urogastone, cetraxate, cimetidine and ranitidine; choleretics such as bile acid; etc.);

(7) Hormones and antihormones (pituitary hormones such as human growth hormone, corticotropin, oxytocin, vasopressin and protirelin tartrate; androgenic hormones such as testosterone; estrogenic hormones such as progesterone and estradiol; salivary gland hormones, thyroid and parathyroid hormones, anabolic hormones, adrenocortical hormones, kallikrein, insulin, chlormadinone acetate, desmopressin acetate, etc.), oxendolone, etc.;

(8) Drugs for urogenital organs (oxytocics such as dinoprost and dinoprostone; etc.);

(9) Metabolic drugs (vitamins such as alfacalcidol and mecobalamine; nutrients, tonics and alteratives; glutathione, ATP, aprotinin, gabexate mesylate, etc.);

(10) Cell activators;

(11) Antitumor drugs (Krestin, ancitabine, cytarabine, Picibanil, 5-fluorouracil derivatives inclusive of tegafur and carmofur, etc.);

(12) Chinese medicines (licorice, aloes, etc.);

(13) Antibiotics (ampicillin, amoxicillin, erythromycin, dibekacin, gentamicin, amikacin, cefazolin, griseofulvin, tetracycline, nystatin, amphotericin B, cycloserine, fosfomycin, peptide antibiotics, etc.);

(14) Chemotherapeutic agents (clotrimazole, pyrrolnitrin, alafosfalin, sulfa drugs, etc.); and (15) Enzymes (urokinase, bromelains, lysozyme, L-asparaginase, etc.).

Among the drugs such as mentioned above, those which are low in bioavailability especially when administered by the oral route (e.g., drugs selected from the above (1), (4) to (7), (13), (15), etc.) or those which can be administered only by injection (e.g. drugs selected from the above (2), (7), (11), (13), (15), etc.) are effectively employed as the efficacy ingredients of the soft buccals according to the present invention.

In the practice of the present invention, the above drugs are used in an amount sufficient to produce their efficacy. In most cases, the drugs are used in an amount of 0.05 to 60 percent by weight based on the whole soft buccal weight. For each individual drug, its amount may be increased or decreased within the above range in an adequate manner depending on the type of drug and the purpose of therapy or, in other words, depending on whether a small dose is sufficient or a larger dose is required for the drug to produce its effects.

As the water-soluble protein to be incorporated in the soft buccals according to the present invention, there may be used any water-soluble protein capable of promoting the absorption of drugs. Such water-soluble protein includes natural proteins of animal or plant origin and non-natural ones which are artificially-produced peptides. The term "protein" as used herein thus includes peptides in view of their effects in practicing the present invention, although peptides are distinguished from proteins in some technical fields. Natural proteins usable in the practice of the present invention are gelatin, solubilized collagen, casein, glue, and hydrolysates therefrom. Among them, preferred are animal proteins such as gelatin and solubilized collagen. Usable gelatin species have a molecular weight of tens of thousands to hundreds of thousands and include acid process gelatin species and alkali process gelatin species respectively produced by acid and alkali hydrolysis of proteins contained in the bone, skin, tendon and the like of animals. Usable collagen species are solubilization products from insoluble collagen by partial hydrolysis and chemically modified collagen species such as maleic, succinic or phthalic anhydride addition products. Their molecular weight lies in almost the same range as that for the gelatin species. Furthermore, as the above-mentioned peptides usable in the practice of the present invention, there may be mentioned peptides produced by combining amino acids of the same or different kinds by a synthetic or semisynthetic technique. Examples of such peptides are polyalanine, polylysine, polyglutamine and other amino acid homopolymers, and copolymers of different amino acids as produced by combining various amino acids (neutral, basic, acidic) in a desired sequence. In most cases, they have a smaller molecular weight as compared with the above-mentioned natural proteins, for example several hundred to several thousand. In practicing the invention, the above-mentioned water-soluble proteins are used either singly or as a mixture of two or more of them.

The above-mentioned water-soluble protein is incorporated in the soft buccals in an amount sufficient to promote the drug absorption through the oral mucosa. Usually, an amount almost equal to the drug amount is required. However, the protein amount may be decreased or increased depending on the kind of drug and the desired rate of absorption, without any generalized limitation. Generally, the water-soluble protein is incorporated in an amount of 0.5 to 150 parts, preferably about 1 to 100 parts, per part of the drug. When the drug amount in the soft buccals is large, the water-soluble protein is used in an amount of about 0.5 to 10 parts per part of the drug and, when the drug amount is small, the water-soluble protein is used in an amount of about 10 to 150 parts per part of the drug. The amount of the water-soluble protein to be incorporated can be redcued by adding one or more of the additives to be mentioned later so as to fill up the remainder portion of the pharmaceutical preparation.

In accordance with this invention, a pharmaceutically acceptable polyhydric alcohol is used as the third component for the purpose of controlling and maintaining the softness of the soft buccal and, also, of controlling the rate of dissolution or disintegration. The above-mentioned polyhydric alcohol includes, typically and among others, glycols, triols and polyols, for example glycols of 2 to 6 carbon atoms (e.g. ethylene glycol, propylene glycol, butylene glycol), polyethylene glycol (with an average molecular weight of about 200 to 50,000, and preferably of about 300 to 5,000), etc., and triols such as glycerin, trimethylolpropane, etc., and polyols such as polyvinyl alcohol, etc. In addition, cellulose, sugars, etc. also fall within the scope of the polyhydric alcohol that can be employed in the practice of this invention. The cellulose may be one having an average molecular weight of about 13,000 to 400,000 and preferably of about 40,000 to 200,000. Thus, for example, alkyl-and hydroxyalkylcelluloses whose alkyl moieties contain 1 to 4 carbon atoms (e.g. methylcellulose, ethylcellulose, propylcellulose, hydroxymethylcellulose, hydroxyethylcellulose, etc.), and carboxymethyl cellulose and alkali metal (e.g. sodium, potassium, etc.) salts thereof. Typical of said sugars are monosaccharides, disaccharides and polysaccharides. The monosaccharides preferably contain 2 to 6 carbon atoms and include, for example, glucose, galactose, fructose, mannose, mannitol, sorbitol, etc., and the disaccharides may be the dimers of such monosaccharides, for example maltose, lactose, sucrose, etc. The polysaccharides include the genuine polysaccharides which are condensates of at least 7 units of the above-mentioned monosacharides, such as starch and its derivatives (e.g. carboxymethyl-starch, hydroxypropyl-starch), dextrin, dextran, chitin, alginic acid, glycogen, Purlan ® (Hayashibara, K.K. in Japan), etc. and the composite condensates of at least 7 units of one of the above-mentioned monosaccharides with one of non-suger substances such as mannan, pectin, gum arabic, etc. The above-mentioned third component are used either singly or as a mixture of two or more of them. The polyhydric alcohol as the third component is preferably a non-volatile compound and those alcohols giving plasticity such as glycerin are advantegeous in many instances.

The amount of said third component in the soft buccal according to this invention depends on the kind and amount of water-soluble protein used but is generally correlated with the amount of water-soluble protein. Thus, it is generally advantageous to employ about 0.01 to 3 parts, preferably about 0.03 to 2 parts, of the third component for each part of the water-soluble protein.

In the soft buccal preparation according to this invention, the pharmaceutically acceptable fatty acid ester or/and carboxyvinyl polymer as the fourth component is incorporated for the same purpose as in the case of the addition of the above-mentioned third component and also for the purpose of assisting in the development of characteristics of the soft buccal.

The above-mentioned fatty acid ester is a monoalcohol or polyalcohol ester of a saturated or unsaturated fatty acid. More specifically, such ester consists of a saturated or unsaturated fatty acid containing 4 to 30 carbon atoms, preferably 8 to 20 carbon atoms, as the carboxylic acid moiety (the number of double bonds in the unsaturated fatty acid is about 1 to 8) and a monoalcohol or polyalcohol containing 1 to 30 carbon atoms, preferably 1 to 20 carbon atoms, as the ester residue moiety. This polyalcohol may be the same as the above-mentioned polyhydric alcohol but preferably contains about 2 to 10 hydroxy groups (e.g. glycerin, ethylene glycol, propylene glycol, etc.). Examples of the above-mentioned fatty acid ester include alkyl esters of intermediate or higher fatty acids containing 8 to 20 carbon atoms (e.g. isopropyl myristate), and glycerin esters of fatty acids containing 1 to 20 carbon atoms (inclusive of mono-, di- and triglycerides) [e.g. Witepsol® (Dynamit Nobel in West Germany), ODO® (Nisshin Oil Co., Ltd. in Japan)], sucrose fatty acid esters whose fatty acid moieties contain 9 to 30 carbon atoms (e.g. mixtures of mono-, di- and triesters of stearic acid and palmitic acid), etc. The fatty acid esters include not only such monocarboxylic acid esters as mentioned above but also those consisting of a dicarboxylic acid of 4 to 20 carbon atoms and the ester moiety described above (e.g. diisopropyl adipate, diethyl sebacate, etc.).

The carboxyvinyl polymer mentioned above preferably has an average molecular weight of about 40,000 to 3,000,000, and includes polyacrylic acid and polymethacrylic acid and their salts, for instance. As the carboxyvinyl polymer, such commercial products as Hiviswako® (Wako Pure Chemical Industries Ltd. in Japan), Carbopol® (Goodrich in U.S.A.), Lubiscol® (B.A.S.F. in West Germany), etc. can be employed with advantage.

In practicing this invention, it is desirable to choose from among these fourth components one which will contribute best to the above-mentioned purposes and is capable of dispersing or dissolving the medicament. The above-mentioned fourth components are used either singly or as a mixture of two or more of them.

The amount of such fourth component in the soft buccal depends on the kind and amount of said water-soluble protein but is generally correlated with the amount of water-soluble protein. Thus, it is generally advantageous to use about 0.01 to 10 parts, preferably about 0.03 to 7 parts of the fourth component for each part of the water-soluble protein.

In addition to the above components, there may also be incorporated other additives selected from among the various pharmaceutically acceptable additives available to those skilled in the art for the purpose of assisting in the development of characteristics of the soft buccal, of improving the processability, moldability and quality of the preparation, of enhancing the dispersability and stability of the medicament, for instance. Such additives are other than those mentioned as the essential components and include the following substances.

(1) Flavors (saccharin sodium, glycyrrhizin, malt syrup, citric acid, tartaric acid, menthol, lemon oil, citrus flavor, common salt, etc.);

(2) Stabilizers/preservatives (parahydroxybenzoic acid alkyl esters, antioxidants, antifungal agents, etc.);

(3) Colors (water-soluble tar colors, natural colors, titanium oxide, etc.);

(4) Excipients/disintegration adjusting agents (magnesium silicate, light silicic acid anhydride, synthetic aluminum silicate, precipitated calcium carbonate, magnesium aluminum metacilicate, calcium hydrogen phosphate, etc.);

(5) Water-soluble polymers other than water-soluble proteins (nutural polymers, synthetic polymers, etc.) and (6) Stearic acid and its salts, talc, palmitic acid, and other substances known as emulsifiers, dispersants, binders, thickners, etc.

In a typical embodiment in which the above additives are used, there are used, for instance, an emulsifier or dispersing agent for causing uniform dispersion of the drug and water-soluble protein, a flavoring agent for seasoning the soft buccal, a stabilizer or preservative for improving the stability of the soft buccals from the pharmaceutical viewpoint, and a binder or excipient for maintaining the shape of the soft buccals. However, each additive is not always used for one purpose alone.

As the shape of the soft buccals, there may be used any shape which fits the oral or buccal cavity and can be held in said cavity. Accordingly, the soft buccals are given a size and shape which facilitate the application into the oral cavity.

Such form is preferably selected from among sheet form, band form, disk form, pillar form, cylindrical form and spindle form, and in many cases, sheet form (e.g. about 0.5 to 3 cm by about 1 to 10 cm, and about 0.1 to 0.5 cm thick) and disk form (e.g. about 0.2 to 3 cm in diameter and about 0.05 to 0.5 cm thick) are desirable.

The soft buccals according to the present invention have such shape and at the same time are in general soft. The term "soft" as used herein includes, within the meaning thereof, flexibility in the oral cavity as well. To be concrete, the soft buccals have flexibility or softness and viscoelasticity, as seen in the fact that they can be deformed to a certain extent without any damage. For instance, they can easily be bent so as to make almost a right angle or can easily expand or contract or become depressed under the action of a slight external force. In using the soft buccals according to the present invention, they may be deformed in such a manner. They may also be cut prior to use.

For the purpose of maintaining the characteristic features of the preparation, such as softness, dissolvability or disintegrability and drug absorbability, it is generally desirable that the soft buccals according to the present invention contain water. The amount of water to be contained is about 3 to 30 percent by weight, preferably 5 to 20 percent by weight, based on the whole soft buccal weight.

The soft buccals according to the present invention can be produced by various methods. The production techniques available for the conventional tablets or suppositories or for chewing gum species, cakes or noodles, for instance, can be used in the production of the soft buccals according to the present invention with necessary modifications. Said modifications are made for achieving the object of the present invention, namely for providing the buccals with flexibility and improving the absorption of drugs. In a typical process for the production of the soft buccals, the above-mentioned drug, water-soluble protein, third and fourth components are mixed, together with the above-mentioned additives as necessary, and, following addition of a small amount of water, the mixture is kneaded uniformly, compressed and extended while it is warm, and then, after cooling, the resulting sheet is cut. In an alternative process, the above-mentioned drug-protein mixture is pulverized as it is without addition of water and then compression-molded. In a third process, the above-mentioned drug-protein mixture is uniformly dispersed or dissolved in water and thus molded by the wet method, followed by drying. The steps in these production processes may be combined in an adequate manner other than the manners mentioned above. In producing the soft buccals according to the present invention, the drug, water-soluble protein, third and fourth components are used in the amounts prescribed above together with the additives in necessary amounts. In the step of molding or shape adjustment as mentioned above, soft buccals having a desired shape, such as the plate, belt-, disk-, pillar-, cylinder- or spindle-like form, can be obtained by adjusting the mold for compression molding to an appropriate shape or by pouring into a mold or extending the molding compound followed by cutting the premoldings into pieces having an appropriate shape. Such a production method comprises only simple and easy operations and steps and accordingly is an advantageous production method usable on a commercial scale, by which soft buccals in various shapes suited for the purpose in each individual case can be produced depending on the procedure followed. When a step of dissolution or dispersion is included, liquid or low-melting drugs, which are hard to incorporate into solid preparations, can be incorporated into the soft buccals.

The soft buccals according to the present invention are applied to the mucosa within the oral cavity. More specifically, they are held mainly between the gingiva and the cheek or lip. In some instances, they may be applied between the gingiva and the tongue or under the tongue or on the maxillary mucosa. Being soft, the soft buccals according to the present invention feel soft in the oral cavity and therefore can be used without disagreeability. Since, upon application, they swell with the saliva in the mouth or with a product of secretion and show a tendency to adhere to the oral mucosa, they are well held in the oral cavity for a long period without falling off. Therefore, daily-life actions (conversation, eating and drinking, smoking, motions, learning, etc.) are never obstructed. The soft buccals according to the present invention can be produced so that at least 10 minutes, for instance, is required for their dissolution or disintegration in the mouth. In that case, the soft buccals have properties desired of a sustained release preparation and the drug component contained therein is released gradually. There are some cases that the soft buccal containing only the first component (1), second component (2) and third component (3) without the fourth component (4) can have the above-mentioned desired properties. Furthermore, the incorporation of the above-mentioned third and fourth components in addition to the components (1) and (2) produces, among others, the following effects: (1) That incorporation of a drug unsatisfactory in dispersibility or solubility in the preparation (e.g. hardly soluble drug, highly liposoluble drug) becomes facilitated and at the same time uniform dispersion or dissolution thereof becomes possible; (2) That control of those factors which affect the drug release from the preparation onto the mucosa, such as disintegration or dissolution time, wettability with water and rate of penetration of water, becomes possible in a desired way; (3) That manufacture of soft buccals becomes easy since adhesion to preparation-making apparatus does not occur any more; (4) That preparations durable upon long-term storage and good in stability (e.g. free from deformation or deterioration) can be obtained; and (5) That preparations excellent in adhesion and easily applicable to the oral mucosa or tongue without using water can be obtained.

The soft buccal preparation according to the present invention is a preparation for oral cavity application which is markedly improved in the drug absorption through the mucosa as well as the sustained releasability mentioned above. Thus, the drug released is absorbed efficiently through the oral mucosa and esophageal mucosa, so that the bioavailability of the drug is improved. Therefore, the expected pharmacological effects can be produced in a smaller dose of the drug. At the same time, the possible adverse effects can be reduced and the safety increased through avoidance of overdosage of the drug. In particular, those drugs which, when in the dosage form for oral administration, are unsatisfactorily absorbed through the gastrointestinal tract and are poor in bioavailability, or which, when absorbed through the gastrointestinal tract, are rapidly metabolized and as a result rapidly lose their efficacy and are poor in bioavailability when orally administered, or which are liable to decomposition in the gastrointestinal tract or to the first pass effect in the liver and therefore are not orally administrable (or can be orally administered without effects) but can be administered only parenterally can easily be administered in the soft buccal form in accordance with the present invention to give a high level of bioavailability. For instance, it has been found, as is detailedly described hereinafter in the test examples, that when a drug is administered in the soft buccal form according to the invention, an at least doubled blood level is attained as a result of rapid absorption of the drug through the mucosa and the blood level is maintained for a prolonged period of time as compared with the conventional preparation for oral administration or sublingual tablet form. Furthermore, it has also been demonstrated that even a drug which can be absorbed and produce its efficacy only in the form of injection can be absorbed to a satisfactory extent when applied in the soft buccal form according to the invention.

Various advantages of the soft buccals according to the present invention as mentioned above (good feeling in use, good retainability within the mouth, slow release, improved absorbability of drug through the mucosa, improved bioavailability, etc.) are offered mainly by the incorporation of a water-soluble protein as one of base components as well as the incorporation of the above-mentioned third and fourth components. Although various uses of water-soluble proteins are known in the art, there is no precedent for the use thereof as an essential constituent of a base for oral cavity preparations. The advantage of such use has been shown for the first time by the present inventors.

The following more detailed description of the methods of producing the soft buccals according to the invention and the results of various tests will further illustrate the invention.

EXAMPLE 1

Riboflavin tetrabutyrate-containing soft buccals (a) Riboflavin tetrabutyrate (2.4 g) was added to a solution composed of 30 g of purified water, 16 g of concentrated glycerin and 0.8 g of Ryoto Sugar Ester ®S-770, a sucrose fatty acid ester distributed by Ryoto K.K. in Japan. The mixture was stirred to give a homogeneous suspension. Thereto was added a solution prepared by dissolving 32 g of gelatin (jelly strength: 150) in 50 g of purified water at 50° C. Using a vacuum stirrer, the whole mixture was stirred and at the same time defoamed while preventing the evaporation of water until a homogeneous mixture was obtained. While it was warm (about 40° C.), the mixture was poured into a mold (10×20×0.3 cm) and spread uniformly. After cooling, the plate-like primary preparation was cut, using a cutter, into pieces each having a size corresponding to a single dosage form. Each piece contained 60 mg of riboflavin tetrabutyrate, weighed 3.28 g (deviation: within ±0.5%) and had a plate-like shape [1.5×6.3×0.3 cm (length×breadth×thickness)]. The pieces were air-dried at 25° C. for about 2.5 hours to give soft buccals in the final form (the weight of each buccal: 2.2 g).

(b) In the step of spreading in the above process (a), spreading was conducted to a greater thickness (about 0.7 cm). After cooling, the primary preparation was punched to give cylindrical pieces (0.7 cm in diameter×7.3 cm in length), which were then dried. There were obtained cylinder-shaped soft buccals.

(c) To 1.8 g of riboflavin tetrabutyrate, there were added 4.5 g of concentrated glycerin, 1.5 g of WITEPSOL® (trademark; Dynamit Nobel) and 0.12 g of Ryoto Sugar Ester ®S-970 a sucrose fatty acid ester distributed by Ryoto K.K. in Japan. The mixture was mixed at about 70° C. To the resulting uniform mixture, there were added 16.2 g of gelatin, 1.2 g of sorbitol, 0.03 g of methylparaben and 0.015 g of propylparaben, followed by further addition of 2.84 g of purified water. The whole mixture was kneaded until it became homogeneous and then compressed and uniformly extended at about 70° C. using a molding roll. After cooling, the primary preparation obtained was cut to a size corresponding to a single dosage form. Each buccal contained 60 mg of riboflavin terabutyrate, weighed about 900 mg (deviation: within ±2%) and had a plate-like shape (length×breadth×thickness: 1.0×4.0×0.2 cm).

EXAMPLE 2

Oxendolone-containing soft buccals (a) To 1.5 g of oxendolone, there were added 3.75 g of concentrated glycerin, 1.2 g of ODO ®, a commercially available medium-chain fatty acid triglyceride distributed by Ryoto K.K. in Japan (Nisshin Oil Co., Ltd), and 0.12 of a sucrose fatty acid. The mixture was stirred at about 70° C. until it became homogeneous. Thereto were added 15 g of gelatin, 1.2 g of sorbitol, 0.03 g of methylparaben and 0.015 g of propylparaben, followed by further addition of 2.1 g of purified water. The whole mixture was kneaded until it became homogeneous. The mixture was compressed in a metal mold with warming (at about 65° C.). After cooling, the plate-shaped primary preparation was taken out of the mold and cut into pieces each having a size corresponding to a single dosage form. Each buccal contained 50 mg of oxendolone, weighed about 320 mg (deviation: within ±2%) and had a plate-like shape [1.0×3.5×0.2 cm (length×breadth×thickness)].

(b) To 1 g of oxendolone, there were added 2.5 g of concentrated glycerin, 0.8 g of cacao butter and 0.08 g of a sucrose fatty acid ester (Ryoto Sugar Ester ®S-770). The mixture was stirred at about 70° C. until uniformity resulted. Thereto were added 9 g of gelatin, 0.8 g of sorbitol, 0.02 g of methylparaben and 0.01 g of propylparaben, followed by kneading. Separately, a solution 0.02 g of dipotassium glycyrrhizate in 1.57 g of purified water was prepared and added to the above kneaded mixture. The whole mixture was stirred uniformly and further kneaded and, then, compressed and spread uniformly by means of a metallic molding roll while warming at about 70° C. After cooling, the primary preparation obtained was cut to a size corresponding to a single dosage form. Each buccal thus obtained contained 50 mg of oxendolone, weighted about 800 mg (deviation: within ±2.0%) and had a plate-like shape [1.0×3.2×0.2 cm (length×breadth×thickness)].

(c) To 1 g of oxendolone, there were added 2.25 g of concentrated glycerin, 0.72 of WITEPSOL®(H-15) and 0.072 g of Ryoto Sugar Ester ®S-770 a sucrose fatty acid ester product distributed by Ryoto K.K. of Japan. The mixture was stirred at about 70° C. until it became homogeneous. Thereto were added 9 g of gelatin, 0.9 g of sorbitol, 0.018 g of methylparaben and 0.010 g of propylparaben, followed by kneading. Separately, a solution of 0.020 g of dipotassium glycyrrhizate and 0.18 g of sodium chloride in 1.4 g of purified water was prepared and added to the above kneaded mixture. The whole mixture was stirred and kneaded until it became homogeneous. Then, the mixture was compressed uniformly extended by means of a molding roll under warming (at about 70° C.). After cooling, the primary preparation obtained was cut to a size corresponding to a single dosage form. Each buccal thus obtained containing 50 mg of oxendolone, weighted about 750 mg (deviation: within ±2.0%) and had a plate-like shape [0.8×30.2 cm (length×breadth×thickness)].

EXAMPLE 3

Dihydroergotamine methanesulfonate-containg soft buccals

Dihydroergotamine methanesulfonate (1 g) and 9 g of gelatin (jelly strength: 150) were mixed and pulverized in a vibrating ball mill for an hour. [The pulverized mixture did not show any endothermic peak ascribable to dihydroergotamine methanesulfonate on a differential scanning colorimeter (DSC).] Then, 5 g of concentrated glycerin, 10 g of lactose and 30 g of thick malt syrup powder were added, and the whole mixture was stirred and blended in an automatic mortar for 10 minutes. Furthermore 55-mg portions of the mixture (each portion corresponding to a single dosage form) were compression-molded in a metal mold using a hydraulic press to give plate-shaped soft buccals each containing 1 mg of dihydroergotamine methanesulfonate and having a size of 0.8×1.0×0.2 cm (length×breadth×thickness).

EXAMPLE 4

Ubidecarenone-containing soft buccals

Ubidecarenone (10 g) and 90 g of gelatin (jelly strength: 180) were mixed and pulverized in a vibrating ball mill to give a mixture with the endothermic peak due to ubidecarenone being no more detected. Thereto were added 25 g of concentrated glycerin and 25 g of lactose. After thorough mixing, the mixture was made into cylinder-shaped soft buccals (7.5 mm in diameter and 2.5 mm in thickness; each weighing 150 mg) each containing 10 mg of ubidecarenone by the method of producing tablets as described in the Japanese Pharmacopeia, 10th edition (JP X) under the General Rules for Preparations.

EXAMPLE 5

Lysozyme chloride-containing soft buccals

Lysozyme chloride (10 g) and 90 g of gelatin were mixed and pulverized in a vibrating ball mill for 30 minutes. Then, 20 g of concentrated glycerin, 10 g of lactose and 20 g of mannitol were added, and the whole was mixed uniformly. Thereafter, the mixture was processed in the same manner as in Example 4 to give cylinder-shaped soft buccals (8 mm in diameter and 2 mm in thickness; weighing 150 mg) each containing 10 mg of lysozyme chloride.

EXAMPLE 6

Triamcinolone acetonide-containing soft buccals (a) Concentrated glycerin (17.0 g) was added to 0.25 g of triamcinolone acetonide, and dispersion was effected by ultrasonic treatment for about 20 minutes. This dispersion and 50 g of medium-chain fatty acid triglyceride (ODO ® brand, Nisshin Oil Co.) were added to a homogeneous mixture of 699.75 g of gelatin (jelly strength: 180) and 80 g of Atmul ®T-95, a glycerin fatty acid ester product distributed by Kao Food K.K., and the resultant mixture was stirred and further kneaded. The mixture was then uniformly compressed and extended by means of a metallic molding roll while warming the mixture (at about 70° C.). After cooling, the primary preparation obtained was cut into pieces each having a size corresponding to a single dosage form. Each piece (i.e. buccal) contained 0.025 mg of triamcinolone acetonide, had a plate-like shape (length×breadth×thickness: 0.5×1.0×0.55 cm) and weighed about 100 mg (deviation in weight: within ±2%). The disintegration time as measured by the method described in JP X was about 38.5 minutes (35 to 41 minutes).

(b) To 0.25 g of triamcinolone acetonide, there were added 70 g of medium-chain fatty acid triglyceride mixture containing 2.5% of soybean lecithin and 120 g of concentrated glycerin, and dispersion was effected by ultrasonic treatment for about 5 minutes. The dispersion was added to a mixture of 608.25 g of gelatin (jelly strength: 210), 20 g of mannitol, 100 g of 1% aqueous solution of HIVISWAKO ®104 (a commercially available carboxyvinyl polymer product distributed by Wako Pure Chemical Industries Ltd., viscosity: about 85,000 cps), 1.5 g of ethylparaben and 250 g of purified water. The whole was mixed until it was uniform and, then, 150 g of corn starch was further added, followed by stirring and kneading. The resultant mixture was uniformly compressed and extended by means of a molding roll while warming the mixture at about 70° C. After cooling, the primary preparation was punched so as to give pieces each having a size corresponding to a single dosage form, namely a disk-like shape (10.5 mm in diameter, 1.55 mm in thickness). Each buccal thus obtained contained 0.025 mg of triamcinol-one acetonide and weighted about 150 mg (deviation: within ±2%).

EXAMPLE 7

Dihydroergotoxine mesylate-containing soft buccals (a) Dihydroergotoxine mesylate (10 g), 200 g of purified water, 120 g of concentrated glycerin and 250 g of gelatin were placed in a reduced-pressure mixer stirrer. After about an hour of standing for swelling, the whole charge was mixed with warming (at about 70° C.) while preventing evaporation of water, until it was homogeneous. Then, after the temperature was lowered to 50° C., 80 g of corn starch was added, followed by kneading. The resultant mixture was extruded through a pump quantitatively and molded into a sheet having a definite thickness by means of a molding roller. From the sheet, there were obtained, by means of two die rolls, disk-shaped soft buccals (10 mm in diameter, about 1.2 mm in thickness). Each buccal weighed 100 mg (deviation: within ±5%). When the buccal was applied into the mouth, about 45 minutes was required for its dissolution to be almost complete.

(b) A reduced-pressure mixer stirrer was charged with 10 g of dihydroergotoxine mesylate, 200 g of purified water, 150 g of concentrated glycerin, 20 g of MACROGOL 4,000 (PEG-4,000) and 200 g of gelatin. After about an hour of standing for swelling at room temperature, the charge was mixed under reduced pressure with warming (about 70° C.) while preventing evaporation of water, until the whole mixture was homogeneous. The, 320 g of mannitol was added, and the mixture was stirred well. Thereafter, the temperature was lowered to 50° C., and 100 g of corn starch was added, followed by kneading. The kneaded mixture was treated in the same manner as in the above-mentioned Example 7-(a) to give disk-shaped soft buccals (11 mm in diameter, 1 mm in thickness). Each buccal weighted 100 mg (deviation: within ±5%).

EXAMPLE 8

Pindolol-containing soft buccals (a) To 15 g of gelatin was added 33.75 g of purified water, and the gelatin was dissolved with warming at 80° C. and defoaming treatment. To the solution, there was added a dispersion prepared by ultrasonic treatment of a mixture of 3 g of pindolol, 10.5 g of propylene glycol and 0.75 g Ryoto Sugar Ester ®S-570, a sucrose fatty acid ester product distributed by Ryoto K.K. The whole mixture was defoamed with warming and stirring and, then, poured into a mold and extended while it was warm. After cooling, the primary preparation was cut into pieces by means of a cutter so that each piece weighed 630 mg (corresponding to a single dosage form). The pieces were further air-dried (27° C., 20 hours). Each piece (or soft buccal) has a plate-like shape (length×breadth×thickness=about 17×9×2 mm), weighed 310 mg (deviation: within ±2%) and contained 30 mg of pindolol. The disintegration time (JP X) was 12 minutes and 17 seconds (10 minutes and 30 seconds to 12 minutes and 40 seconds).

(b) A mixture of 1.5 g of pindolol, 11.75 g of phosphate buffer (pH 6.5) containing 80% of propylene glycol, 0.75 g of medium-chain fatty acid triglyceride containing 2.5% of soybean lecithin, and 0.5 g of Ryoto Sugar Ester ®S-570 a sucrose fatty acid ester product distributed by Ryoto K.K., was sonicated to give a homogeneous dispersion. The dispersion was added to a homogeneous mixture of 7.5 g of gelatin, 1 g of concentrated glycerin and 3 g of mannitol. The whole mixture was stirred and kneaded (with addition of 2 g of corn starch) with warming (about 70° C.). The resultant mixture was compressed and extended by means of a molding roller with warming at about 50° C. The primary preparation thus obtained was cut into pieces each corresponding to a single dosage form (plate-shaped soft buccal containing 30 mg of pindolol). The disintegration time (JP X) was 16 minutes and 35 seconds (16 minutes to 17 minutes and 15 seconds).

EXAMPLE 9

Allantoin-containing soft buccals (a) A mixture of 50 g of gelatin (jelly strength: 280), 70 g of concentrated glycerin and 74.15 g of purified water was warmed to 50° C. with stirring to make a uniform solution, followed by defoaming treatment (about 2 hours was required). Thereto was added a suspension of 108.5 g of finely divided allantoin in 30 ml of water. The whole mixture was stirred well for about 10 minutes. In the same manner as in Example 1-(a), the resulting uniform mixture was subjected to the steps of molding, cooling and drying to give plate-like soft buccals (length × breadth × thickness: about 1.4 × 7.0 × 0.3 cm) each containing 217 mg of allantoin.

(b) In the step of pouring into the mold in the above process (a), a mold for giving a cylindrical form was used. After cooling, cylindrical moldings (0.7 cm in diameter × 7.6 cm in length) were taken out and dried to give cylindrical soft buccals.

EXAMPLE 10

Pindolol-containing soft buccals (a) Pindolol (1.08 g) was suspended in 18.92 g of purified water with stirring, followed by addition of 6 g of concentrated glycerin and 10 g of gelatin (jelly strength: 150). The resulting mixture was stirred at 70° C. for 3 hours while preventing the evaporation of water, then defoamed under reduced pressure, and poured into a mold while warm and processed by the same manner as in Example 1-(a) to give plate-shaped soft buccals each containing 30 mg of pindolol.

(b) Pindolol (15 g) and 135 g of gelatin (jelly strength: 180) were pulverized in a vibrating ball mill for 2 hours, followed by further addition of 50 g of concentrated glycerin and mixing and pulverizing. Thereafter, 200-mg portions of the mixture (each portion corresponding to a single dosage form) were compressed and molded to give cylinder-shaped soft buccals each containing 15 mg of pindolol.

EXAMPLE 11

Dipyridamole-containing soft buccals

Using 50 g of gelatin (jelly strength: 150), 2.375 g of dipyridamole, 40 g of concentrated glycerin, 0.5 g of sodium polyacrylate and 100 g of purified water and following the procedure of Example 10-(a), there were produced plate-shaped soft buccals each containing 2.5 mg of dipyridamole

EXAMPLE 12

Oxendolone-containing soft buccals (a) Oxendolone was turned into fine crystals by dispersing a solution of oxendolone in a small amount of ethanol in water with stirring. After drying, a 5-gram portion thereof was weighed and dispersed in 45 ml of water. To the suspension were added 25 g of concentrated glycerin and 25 g of gelatin (jelly strength: 150), and the whole mixture was heated at 70° C. with stirring for 2.5 hours while preventing the evaporation of water. After the subsequent defoaming treatment, the mixture was processed in the same manner as in Example 1-(a) to give plate-shaped soft buccals length × breadth × thickness (1.6 × 1.6 × 0.3 cm) each containing 50 mg of oxendolone. The mean buccal weights before and after drying were 1.015 g and 0.695 g, respectively.

(b) Oxendolone (2.5 g) and 22.5 g of gelatin (jelly strength: 180) were pulverized in a vibrating ball mill for 2 hours. Then, 10 g of concentrated glycerin was added and the pulveriziation was continued for about 6 hours. Thereafter, 350-mg portions each corresponding to a single dosage form were compressed and molded to give cyclinder-shaped soft buccals each containing 25 mg of oxendolone.

EXAMPLE 13

Dihydroergotamine methanesulfonate-containing soft buccals (a) To 1 g of dihydroergotamine methanesulfonate, there were added 9 g of concentrated glycerin, 0.5 g of sucrose mono-stearate and 50 g of purified water, and the mixture was stirred to give a homogeneous suspension. Thereto was added 20 g of gelatin (jelly strength: 150), which was dissolved with warming (70° C.). The mixture was then subjected to defoaming treatment using a vacuum stirrer while preventing the evaporation of water and, thereafter, poured into a mold while warm (about 50° C.) and extended uniformly. The primary preparation obtained after cooling was cut into pieces each having a size corresponding to a single dosage form. Each piece contained 1 mg of dihydroergotamine methanesulfonate, weighed 80 mg (deviation: within ±2%) and had a plate-like shape of 0.5 × 0.5 × 0.3 cm (length × breadth × thickness). The pieces were air-dried at 25° C. for about 10 hours to give soft buccals in the final form (each weighing 35 mg).

EXAMPLE 14

The pulverized mixture as obtained in Example 3 was compression-molded on a rotary tableting machine to give cylinder-shaped soft buccals (3.0 mm in diameter, 1.5 mm in thickness; weighing 10 mg) each containing 1 mg of dihydroergotamine methanesulfonate.

EXAMPLE 15

Ubidecarenone-containing soft buccals

Ubidecarenone (0.5 g) was dispersed in 54.5 g of purified water, followed by addition of 15 g of concentrated glycerin, 0.5 g of isopropyl myristate and 30 g of gelatin (jelly strength: 150). The mixture was stirred with warming at 70° C. for an hour while preventing the evaporation of water, followed by defoaming treatment under reduced pressure. While warm, the mixture was poured into a mold. Thereafter, the procedure of Example 1-(a) was followed to give soft buccals each containing 10 mg of ubidecarenone, having a plate-like shape of 1.5 × 3.0 × 0.3 cm (length × breadth × thickness) and weighing 2 g (deviation: within ±0.1%). They were given the final form by air-drying at 25° C. for about 4 hours (each buccal weighing 1.2 g).

EXAMPLE 16

To 100 g of the pulverized mixture as obtained in Example 4, there was added 25 g of concentrated glycerin. The mixture was made uniform in a mortar, and 125-mg portions thereof (each corresponding to a single dosage form) were weighed and molded under pressure in a metal mold under warming at 50° C. After cooling and release from the mold, there were obtained plate-shaped soft buccals [1.2 × 1.5 × 0.2 cm (length × breadth × thickness)] each containing 10 mg of ubidecarenone.

EXAMPLE 17

Nifedipine-containing soft buccals (a) To 1.0 g of nifedipine, there were added 10 g of concentrated glycerin, 1.2 g of Witepsol ® and 34 g of purified water, followed by stirring to cause uniform dispersion. To the thus-obtained suspension was added 15 g of gelatin (jelly strength: 180). The whole mixture was warmed at 70° C. until the gelatin was dissolved. The resulting homogeneous mixture was defoamed while preventing the evaporation of water and, then, while warm (about 50° C.), the mixture was poured into a mold. Thereafter, the procedure of Example 1-(a) was followed to give plate-shaped soft buccals [1.0×1.5×0.3 cm (length×breadth×thickness)] each containing 10 mg of nifedipine and weighing 600 mg (deviation: within ±1.0%). They were given the final form by air-drying at 25° C. for 8 hours (each buccal weighing 300 mg).

(b) Nifedipine (5 g), 0.5 g of Carbopol ®941 and 45 g of gelatin (jelly strength: 150) were mixed and pulverized in a vibrating ball mill for 4 hours and, following further addition of 25 g of concentrated glycerin, the mixing was continued for 30 minutes. Then, 150-mg portions (each corresponding to a single dosage form) were weighed and thereafter processed in the same manner as in Example 16 to give soft buccals each containing 10 mg of nifedipine.

(c) The pulverized mixture as obtained in Example 17 was made into cylinder-shaped soft buccals (6.5 mm in diameter and 2.3 mm in thickness; each weighing 100 mg) each containing 10 mg of nifedipine by the method of producing tablets as described in the General Rules for Preparations of the JP X.

EXAMPLE 18

Lysozyme chloride-containing soft buccals

Gelatin (45 g; jelly strength: 150) was dissolved in 79 g of purified water. To the solution were added 1 g of lysozyme chloride, 1.5 g of diisopropyl adipate and 25 g of concentrated glycerin with stirring to give a homogeneous solution. This was defoamed under reduced pressure while preventing the evaporation of water. While it was warm, the mixture was poured into a mold and thereafter processed in the same manner as in Example 1-(a) to give plate-shaped soft buccals (length×breadth×thickness=1.2×2.0×0.3 cm; weighing 1.5 g; deviation in weight: within ±1%) each containing 10 mg of lysozyme chloride. The soft buccals were given the final form by air-drying at 25° C. for about 5 hours (each buccal weighing 0.9 g).

EXAMPLE 19

To 5 g of the pulverized mixture as obtained in Example 5, there was added 5 g of concentrated glycerin, followed by mixing in a mortar. 330-mg portions (each corresponding to a single dosage form) of the resultant homogeneous mixture were weighed and processed in the same manner as in Example 16 to give plate-shaped soft buccals each containing 30 mg of lysozyme chloride.

TEST EXAMPLE 1

(a) For evaluating the effect of addition of fatty acid glyceride, the soft buccals obtained in Example 6-(a) and 6-(b) were fixed on a slightly wetted glass sheet by pressing them to said sheet and immersed in purified water. The process of swelling and penetration of water was observed and recorded by photographing at timed intervals.

Swelling progressed regularly from the circumference of the buccals to the center thereof. About 4 hours later, the volume was about 1.8 times the original volume, and the periferabl swollen portion had a thickness of about 4–5 mm.

(b) Two soft buccal species containing a colorant (Food Color Red No. 2, aluminum chelate) in place of triamcinolone acetomide were tested in the same manner. One species (1) contained and the other (2) did not contain the fatty acid glyceride.

With the soft buccals (2) containing no fatty acid ester, the dissolution behavior of the colorant with the progress of swelling was very irregular, whereas, with the fatty acid ester-containing buccals (1), the behavior was regular.

From the above, the superiority of the soft buccals with fatty acid glyceride added was confirmed.

TEST EXAMPLE 2

Comparison in bioavailability of pindolol-containing preparations (rabbit serum concentration)

(a) Samples and method of administration

The soft buccals (A) obtained in Example 8-(a) and sublingual tablets (B) obtained by the method described in JP X were sublingually administered to male albino rabbits fasted for 24 hours (weighing 2.6–2.7 kg, in groups of 3 animals) (dose: 10 mg/kg). The tongue was immobilized with a vinyl tube and tape so as to prevent the buccals from being swallowed. Separately, a homogeneous pindolol suspension in 1% carboxymethylcellulose was orally adminietered using a catheter (dose: 10 mg/kg).

(b) Assay method

Blood samples (sample size: 5 ml) were taken at 0.25, 0.5, 1.0, 2.0, 4.0 and 6.0 hours after administration of the above-mentioned preparations (A), (B) and (C), respectively, and centrifuged to separate the serum. Using 2 ml of the serum, the serum level of unchanged pindolol was determined by the fluorometric method according to the description in the literature [Pacha: Experientia, vol. 25, page 802 (1969)]. The results obtained are shown in Table 1.

On the other hand, using 0.5 ml of the serum, pindolol glucuronide was converted to pindolol with $\beta$-glucuronidase (Sigma; G-0501), followed by assay for serum level by the above assay method. The results obtained are shown in Table 2. Sulfate conjugate could not be detected.

(c) Results and discussion

As seen in Table 1, the rise in serum level was remarkable in the oral cavity administration groups (A and B) as compared with the oral administration group (C). In the ordinary sublingual tablet group (B), the absorption at the early stage following administration was slow and the serum level was not persistent, although the level was transitorily high. On the contrary, when the soft buccals according to the present invention were administered, pindolol was rapidly absorbed after administration, and the serum level remained high for a long period. The level was high even after 6 hours.

Furthermore, as seen in Table 2, it was confirmed that the course of change in serum level of glucuronide after administration of the soft buccals (A) according to the invention well reflects the course of change in unchanged pindolol level mentioned above.

Furthermore, in comparison of AUC (area under serum level curve; ng·min·ml$^{-1}$×10$^4$, hour 0 to hour 6) values, the soft buccals according to the invention exhibited a higher value than those for the other preparations.

TABLE 1

| | Serum level of pindolol (rabbit: ng/ml) | | | | | | AUC (ng. min. ml$^{-1}$ × 10$^4$) |
|---|---|---|---|---|---|---|---|
| | Duration after administration (hr) | | | | | | |
| Preparation | 0.25 | 0.5 | 1.0 | 2.0 | 4.0 | 6.0 | 0–6 hr |
| (A) | 23 ± 9 | 46 ± 13 | 114 ± 47 | 119 ± 22 | 81 ± 16 | 39 ± 7 | 2.93 ± 0.19 |
| (B) | 13 ± 2 | 26 ± 6 | 37 ± 11 | 109 ± 29 | 32 ± 9 | 19 ± 2 | 1.72 ± 0.43 |
| (C) | 27 ± 11 | 25 ± 3 | 24 ± 4 | 17 ± 2 | 15 ± 2 | 5 ± 3 | 0.57 ± 0.02 |

TABLE 2

| | Serum level of pindolol glucuronide (rabbit: ng pindolol eq./ml) | | | | | | AUC (ng. min. ml$^{-1}$ × 10$^4$) |
|---|---|---|---|---|---|---|---|
| | Duration after administration (hr) | | | | | | |
| Preparation | 0.25 | 0.5 | 1.0 | 2.0 | 4.0 | 6.0 | 0–6 hr |
| (A) | 5 ± 4 | 15 ± 1 | 31 ± 6 | 57 ± 13 | 75 ± 13 | 19 ± 10 | 1.71 ± 0.27 |
| (B) | 0 | 11 ± 5 | 30 ± 16 | 57 ± 5 | 95 ± 59 | 6 ± 6 | 1.85 ± 0.76 |
| (C) | 73 ± 13 | 174 ± 70 | 179 ± 18 | 93 ± 38 | 25 ± 10 | 17 ± 4 | 2.55 ± 0.18 |

TEST EXAMPLE 3

Comparison in bioavailability of pindolol-containing preparations (rabbit serum levels)

(i) Samples and method of administration (A) The soft buccals obtained in Example 10-(a), (B) the soft buccals obtained in Example 10-(b) and (C) sublingual tablets as obtained by the method described in JP X were sublingually administered to male albino rabbits (weighing 2.6 to 2.7 kg; in groups of 3 animals) fasted for 24 hours (the dose being 10 mg/kg). Possible swallowing of the preparations given was prevented by immobilizing the tongue with a vinyl tube and a tape. Separately, a suspension of pindolol in 1% carboxymethylcellulose was orally administered using a catheter (the dose being 10 mg/kg).

(ii) Assay

Blood samples were taken in 5-ml portions at 0.25, 0.5, 1.0, 2.0, 4.0 and 6.0 hours after administration of the above (A), (B), (C) and (D). The serum was separated from each sample by centrifugation. Using 2 ml of the serum, the serum level of the unchanged drug (pindolol) was determined by the fluorimetric method as described by Pacha in Experientia, vol. 25, page 802 (1969). The results obtained are shown in FIG. 1.

Figure 2:
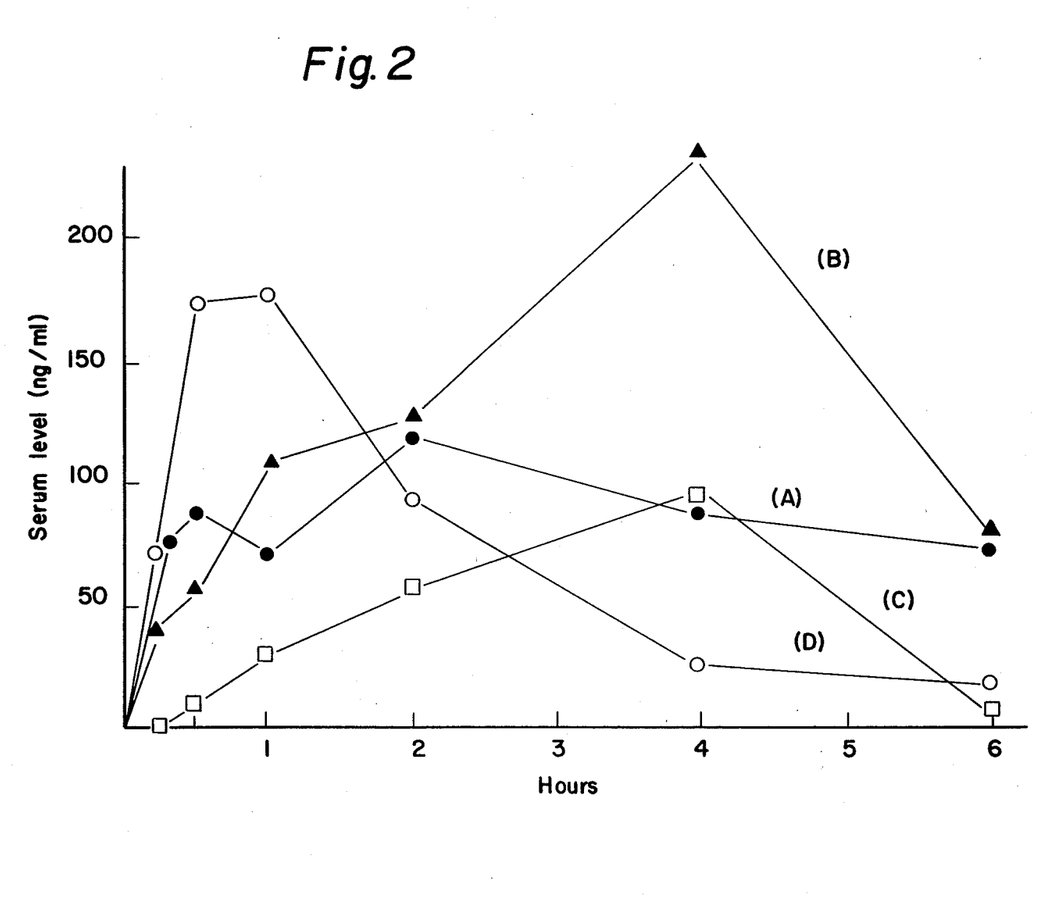

As for the glucuronide of pindolol, 0.5 ml of the serum was used and the glucuronide was converted to pindolol with β-glucuronidase (Sigma; G-0501), and the serum level was determined by the above assay method. The results obtained are shown in FIG. 2. The sulfate conjugate could not be detected.

(iii) Results and discussion

Figure 1:
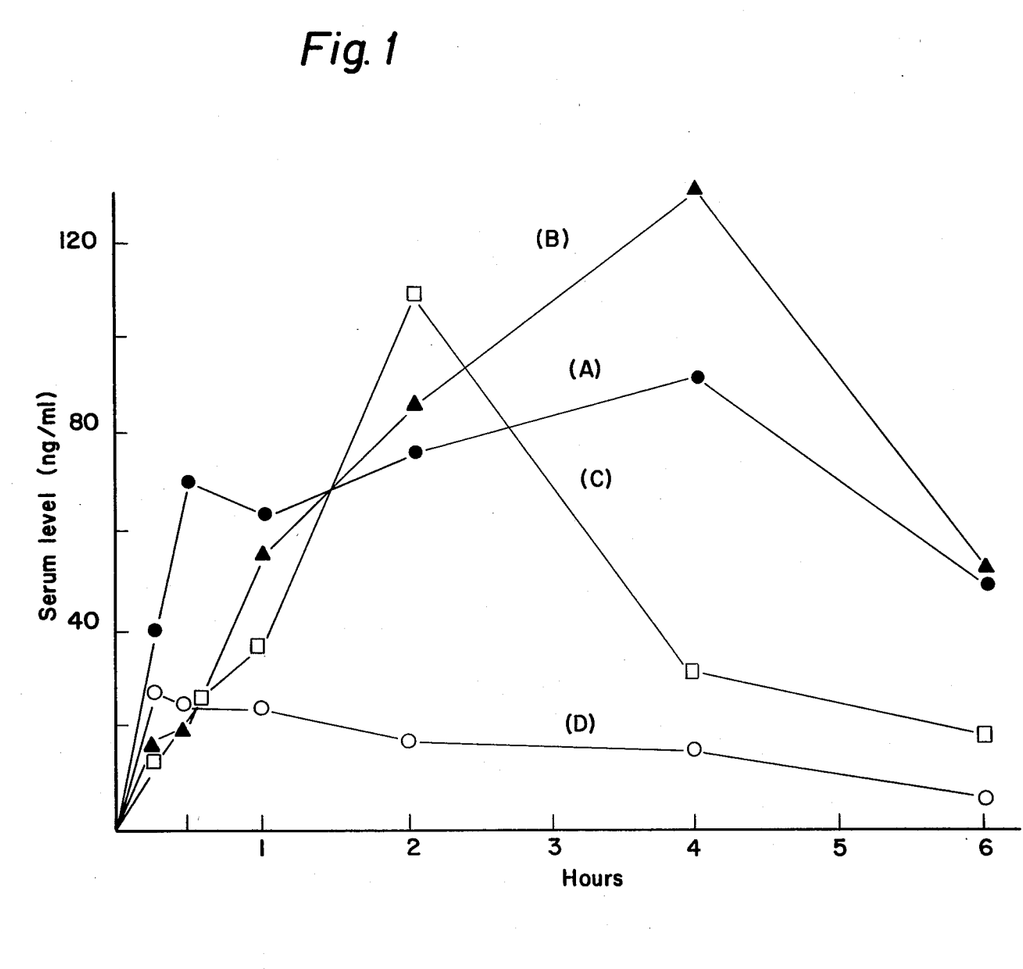

As shown in FIG. 1, the increases in serum level were remarkable in the oral cavity administration groups (A, B and C) as compared with the oral administration group (D). In the usual sublingual tablet group (C), the absorption in the early stage after administration was slow and the drug level was not lasting, although a high level was temporally attained. On the other hand, as for the groups given the soft buccals according to the present invention, pindolol was rapidly absorbed after administration [in group (A)] or absorbed somewhat slowly [in group (B)]. In any case, however, the serum level was sustained and was still high even after 6 hours (not less than about 50 ng/ml on the average). The differences in serum level curve among the preparations were reflected by the differences in AUC (area under the serum level curve; ng·min·ml$^{-1}$ × 10$^4$, 0 to 6 hours) as mentioned below.

(A) 2.59 ± 0.51
(B) 2.99 ± 0.58
(C) 1.72 ± 0.43
(D) 0.57 ± 0.02

Furthermore, it was confirmed, as shown in FIG. 2, that, in the groups given the soft buccals according to the present invention (groups A and B), the serum glucuronide level remained high for long at levels not lower than a certain constant level, well reflecting the above-mentioned course in changes in unchanged drug level. The soft buccals according to the invention gave higher AUC values as mentioned below.

(A) 3.19 ± 0.21
(B) 5.25 ± 0.87
(C) 2.55 ± 0.18
(D) 1.85 ± 0.76

TEST EXAMPLE 4

Comparison in bioavailability of allantoin-containing preparations (plasma levels)

(i) Samples and method of administration

Three normal male adult subjects were given (A) the soft buccals obtained in Example 9 and (B) sublingual tablets as prepared by the method described in JP X at the dose of allantoin of 217 mg/person between the gingiva and the cheek in the oral cavity. (C) Allantoin powder was also administered orally at the dose of 217 mg/person together with 180 ml of water.

The subjects were fasted from the time 12 hours before administration to the time of completion of the test.

(ii) Assay

Blood samples were taken in 3-ml portions before and at 0.5, 1.0, 2.0, 3.0 and 5.0 after administration of the above (A), (B) and (C). The determination of allantoin in plasma was performed by first converting allantoin to allantoic acid by the hydrolyzing method described by R. Borchers et al. in Analytical Biochemistry, vol. 79, page 612 (1977) and then assaying allantoic acid by the method described by P. M. Zarembski et al. in Biochemical Journal, vol. 96, page 218 (1965). The plasma allantoin level after administration of each preparation was calculated by subtracting the allantoin and allantoic acid levels in plasma before administration and the blank value resulting from body constituents from the assay value. The results obtained are shown in FIG. 3.

(iii) Results and discussion

The AUC (area under plasma level curve; μg·hr·ml$^{-1}$, 0 to 5 hours) values were as follows:
(A) 22.55±5.98
(B) 10.48±3.44
(C) 14.51±2.30

Figure 3:
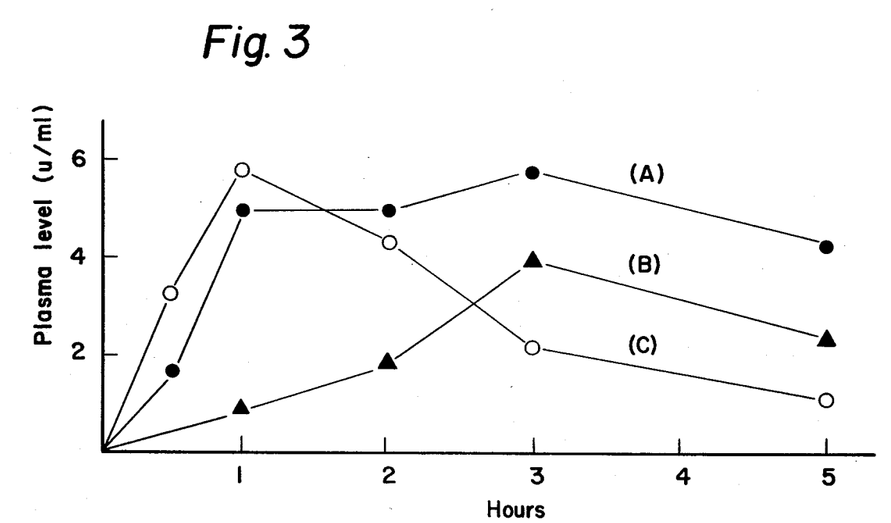

As shown in FIG. 3, the maximum plasma allantoin level ($C_{max}$) after oral administration of (C) was about 6 μg/ml and the time required for the maximum plasma level to be attained ($T_{max}$) was 1 hour. After the administration of the conventional sublingual tablets (B), the rise in plasma allantoin level was very slow. Thus, $C_{max}$ was about 4 μg/ml and $T_{max}$ was 3 hours. It was noted that the rate of absorption was slow as compared with the case of oral administration and the AUC value was rather small as well.

On the contrary, after oral cavity administration of the soft buccals (A) according to the invention, the plasma allantoin level was very similar to that after oral administration (C) in the early stage (0.5 to 1.0 hour after administration) but the subsequent course differed markedly. Thus, whereas the plasma allantoin level after oral administration kept on decreasing when an hour had passed, the plasma level after administration of the soft buccals remained at a relatively constant level (4 to 6 μg/ml) over a period of 1 to 5 hours, indicating the high sustainability of the preparation according to the invention. This fact was also confirmed by the increase in the above-mentioned AUC (about 1.6 times). The soft buccals (A) were better in absorption kinetics in the early stage after administration than the sublingual tablets (B), with $C_{max}$ being high and lasting and the AUC being about 2.2 times that for the sublingual tablets.

TEST EXAMPLE 5

Comparison in bioavailability of oxendolon-containing preparations (dog plasma levels)

(i) Samples and method of administration

Dogs (in groups of 5 animals) faster for 24 hours were given (A) the soft buccals as obtained in Example 12-(a) or (B) the soft buccals as obtained in Example 12-(b) in the oral cavity, or (C) tablets as obtained by the method described in JP X orally, or (D) an injection intramuscularly, the dose being 50 mg/animal in each case.

(ii) Assay

Figure 4:
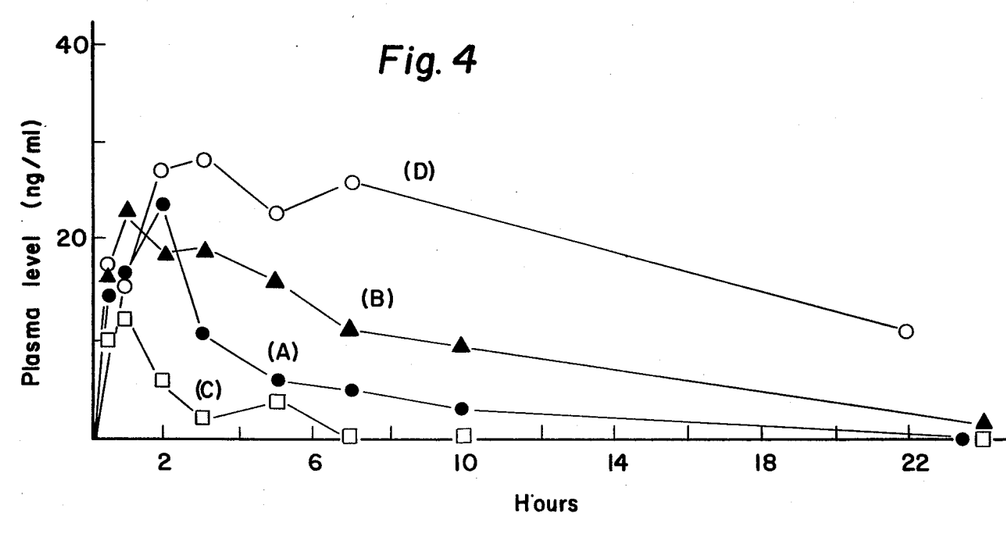

Blood samples were taken at 0.5, 1, 2, 3, 5, 7, 10 and 24 hours after administration of the above (A), (B), (C) and (D), and the plasma was collected from each sample. Using the plasma, the plasma oxendolone level was determined by high performance liquid chromatography according to K. Itakura et al. [J. Takeda Res. Lab., vol. 37, page 297 (1978)]. The results obatined are shown in FIG. 4.

(iii) Results and discussion

The AUC (area under plasma level curve; ng·hr·ml$^{-1}$, 0 to 24 hours) values were as follows:
(A) 120±4
(B) 226±30
(C) 36±22
(D) 500±83

The $C_{max}$ (maximum plasma level, ng/ml) values were found to be 24 for (A), 23 for (B), 12 for (C) and 27 ng/ml for (D).

As can be understood from FIG. 4, it has been proved that the rate of absorption of oxendolone in the early stage after administration of the soft buccals according to the invention (A and B) is rapid with $C_{max}$ being approximately doubled and the level being lasting as compared with oral administration (C). This has also been confirmed by the above-mentioned AUC values; AUC for (A) is 3.3 times and AUC for (B) is even 6.3 times as large as AUC for (C).

Since oxendolone is liable to metabolism in the liver and digestive tract and, when orally administered, gives only low and undurable plasma levels, oral administration thereof cannot be expected to produce satisfactory therapeutic effects. On the contrary, use of the soft buccals according to the invention now can result in promoted absorption and increased and durable plasma level, hence improved bioavailability. Therefore, the soft buccals according to the present invention are expectedly useful as new preparations which can replace the conventional injections.

What we claim is:

1. A soft buccal suitable for retention in the cavity of the mouth particularly suitable for prolonged residence in said cavity due to the softness thereof, said soft buccal containing
   (1) a pharmaceutically effective amount of a medicament to be absorbed through the oral mucosa and to be delivered over the desired residence period of said soft buccal in said cavity;
   (2) a water-soluble protein in an amount of from 0.5 to 150 parts by weight per part of drug (1);
   (3) 0.01 to 3 parts by weight of a polyhydric alcohol per part of protein (2); and
   (4) 0.01 to 10 parts by weight of fatty acid ester or a carboxyvinyl polymer, per part of protein (2).

2. A soft buccal of claim 1 wherein the component (4) comprises a mixture of said fatty acid ester and said carboxyvinyl polymer.

3. A soft buccal base material suitable for accepting a drug, whereby upon incorporation of said drug to form a soft buccal which is capable of retention in the cavity of the mouth, particularly suitable for prolonged residence in said cavity due to the softness thereof, said soft buccal base material comprising
   (a) a water-soluble protein;
   (b) 0.01 to 3 parts by weight of a polyhydric alcohol per part of protein (a); and
   (c) 0.01 to 10 parts by weight of fatty acid ester or a carboxyvinyl polymer, per part of protein (a).

4. A base material of claim 3 wherein the component (c) comprises a mixture of said fatty acid ester and said carboxyvinyl polymer.

5. A method of providing a sustained release of a medicament to a subject which comprises placing a soft buccal of claim 1 in the mouth cavity of said subject, whereby a sustained release of said medicament is delivered to said subject.

6. A soft buccal as claimed in claim 1, wherein the water-soluble protein is at least one selected from gelatin; solubilized collagen; casein; glue; hydrolysates from gelatin, solubilized collagen, casein or glue; polyalanine; polylysine and polyglutamine.

7. A soft buccal as claimed in claim 1, wherein the water-soluble protein is gelatin.

8. A soft buccal as claimed in claim 1, wherein the polyhydric alcohol is at least one selected from glycol, triol and polyol.

9. A soft buccal as claimed in claim 1, wherein the polyhydric alcohol is at least one selected from ethylene glycol; propylene glycol; butylene glycol; polyethylene glycol; glycerin; trimethylolpropane; polyvinyl alcohol; methylcellulose; ethylcellulose; propylcellulose; hydroxymethylcellulose; hydroxyethylcellulose; carboxymethylcellulose or an alkali metal salt thereof; glucose; galactose; fructose; mannose; mannitol; sorbitol; maltose; lactose; sucrose; carboxymethyl-starch; hydroxypropyl-starch; dextrin; dextran; chitin; alginic acid; glycogen; Purlan ®; mannan; pectin; and gum arabic.

10. A soft buccal as claimed in claim 1, wherein the polyhydric alcohol is glycerin or propylene glycol.

11. A soft buccal as claimed in claim 1, wherein the fatty acid ester is a monoalcohol or polyalcohol ester of a saturated or unsaturated fatty acid.

12. A soft buccal as claimed in claim 1, wherein the fatty acid ester is a sucrose fatty acid ester.

13. A soft buccal as claimed in claim 1, wherein the carboxyvinyl polymer is polyacrylic acid, polymethacrylic acid or a salt thereof.

* * * * *

UNITED STATES PATENT AND TRADEMARK OFFICE
CERTIFICATE OF CORRECTION

PATENT NO. : 4,572,832

DATED : February 25, 1986

INVENTOR(S) : Kigasawa et al.

It is certified that error appears in the above-identified patent and that said Letters Patent is hereby corrected as shown below:

On the title assignee should read (73) Assignee: Takeda Chemical Industries., Osaka Japan --.

Signed and Sealed this

Twenty-third Day of December, 1986

Attest:

DONALD J. QUIGG

Attesting Officer     Commissioner of Patents and Trademarks